United States Patent

Brion et al.

Patent Number: 5,556,962
Date of Patent: Sep. 17, 1996

[54] PROCESS FOR THE PREPARATION OF HYDROCORTISONE

[75] Inventors: Francis Brion, Gagny; Jean Buendia, Le Perreux Sur Marne; Christian Diolez, Palaiseau; Michel Vivat, Lagny Sur Marne, all of France

[73] Assignee: Roussel Uclaf, France

[21] Appl. No.: 538,027

[22] Filed: Oct. 2, 1995

Related U.S. Application Data

[62] Division of Ser. No. 362,120, Dec. 22, 1994, Pat. No. 5,502,182, which is a division of Ser. No. 105,742, Aug. 12, 1993, Pat. No. 5,401,840, which is a division of Ser. No. 935,535, Aug. 25, 1992, Pat. No. 5,260,463.

[30] Foreign Application Priority Data

Sep. 6, 1991 [FR] France .................. 91 11052

[51] Int. Cl.⁶ ......................... C07J 21/00
[52] U.S. Cl. ................................ 540/30
[58] Field of Search ........................... 540/30

[56] References Cited

U.S. PATENT DOCUMENTS 4,093,720  6/1978  Rousseau et al. ............. 540/30
5,182,381  1/1993  Philibert et al. ............. 540/30

*Primary Examiner*—Rebecca Cook
*Attorney, Agent, or Firm*—Bierman & Muserlian

[57] ABSTRACT

A compound of the formula

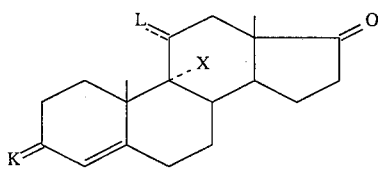

wherein K is a protective group of the oxo of the formula

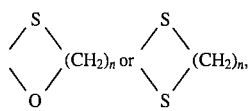

wherein n is 2 or 3 and L is a 11β-hydroxy, the dotted line in the 11-position is not a bond and X is chlorine, bromine or iodine which avoids an 11-hydroxylation step in the preparation of hydrocortisone.

1 Claim, No Drawings

PROCESS FOR THE PREPARATION OF HYDROCORTISONE

PRIOR APPLICATION

This application is a division of U.S. patent application Ser. No. 362,120 filed Dec. 22, 1994 now U.S. Pat. No. 5,502,182, which is a division of U.S. patent application Ser. No. 105,742 filed Aug. 12, 1993, now U.S. Pat. No. 5,401,840 which is a division of U.S. patent application Ser. No. 935,535 filed Aug. 25, 1992, now U.S. Pat. No. 5,260,463.

STATE OF THE ART

European patent No. 30,368 describes a process for the preparation of hydrocortisone which has the problems of low yield and by product formation.

OBJECTS OF THE INVENTION

It is an object of the invention to provide an improved process for the preparation of hydrocortisone and to provide novel intermediates therefor.

This and other objects and advantages of the invention will become obvious from the following detailed description.

THE INVENTION

The novel process of the invention for the preparation of hydrocortisone having the formula

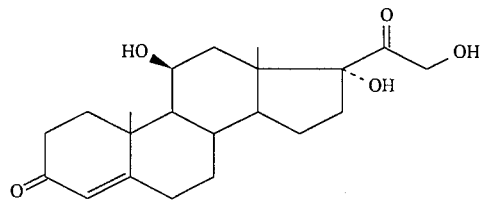

I comprises subjecting a halohydrin of the formula

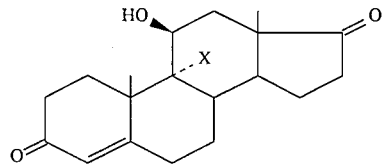

II wherein X is chlorine, bromine or iodine to a rearrangement reaction in the presence of an alcohol to obtain after treatment with an acid a compound of the formula

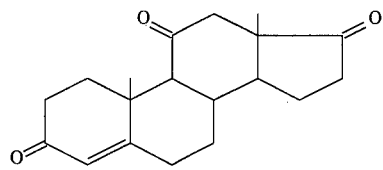

III selectively protecting the 3-oxo function by the action of a thiol or a dithiol of the formula

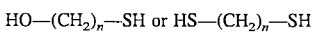

in which n is equal to 2 or 3 to obtain a compound of the formula

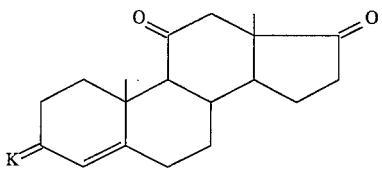

IV wherein K is a protective group of the 3-oxo of the formula

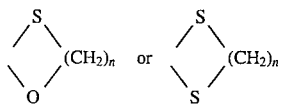

in which n is defined as previously, or a compound of formula II as defined above is treated with a selective blocking agent of the 3-oxo function as defined above to obtain a compound of the formula

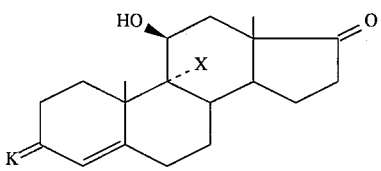

V wherein X and K are defined as above, subjecting the latter to a rearrangement reaction in the presence of an alcohol to obtain, after treatment with an acid, a compound of formula IV as defined above reacting said compound of formula IV with a trihaloacetate of the formula

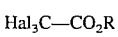

$Hal_3C-CO_2R$ wherein Hal is chlorine or bromine and R is alkyl of 1 to 6 carbon atoms or aralkyl of 7 to 15 carbon atoms or a silyl residue in the presence of zinc and a Lewis acid to obtain a compound of the formula

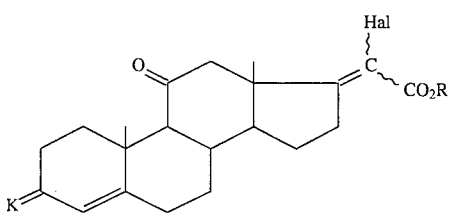

VI wherein K, Hal and R are as defined above, reacting the latter in a basic medium with a phenol of the formula

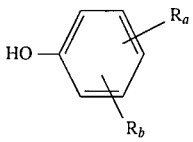

wherein $R_a$ and $R_b$ are individually selected from the group consisting of hydrogen, hydroxy, alkyl and alkoxy of 1 to 4 carbon atoms to obtain a compound of the formula

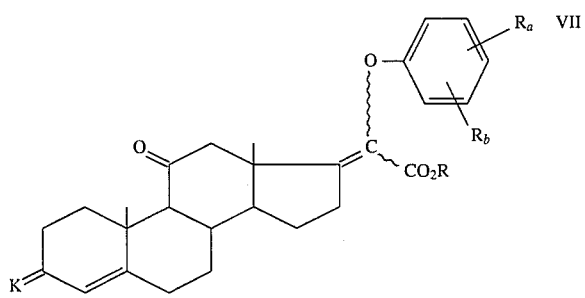

wherein K, R, $R_a$ and $R_b$ are defined as above, reacting the latter with a reducing agent to obtain a compound of the formula

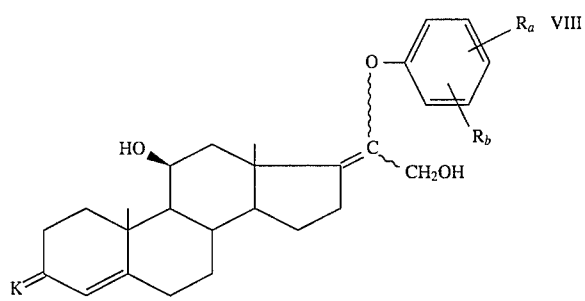

wherein K, $R_a$ and $R_b$ are defined as above, deprotecting the 3-oxo function to obtain a compound of the formula

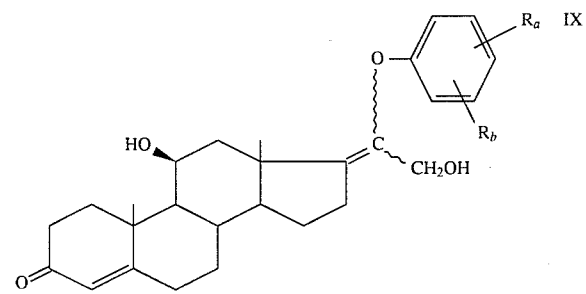

wherein $R_a$ and $R_b$ are defined as above, reacting the latter with an epoxidation agent to obtain a compound of the formula

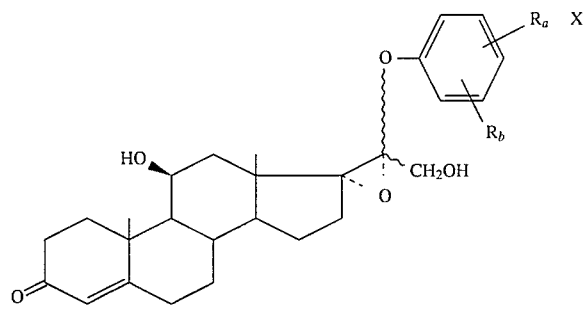

wherein $R_a$ and $R_b$ are defined as above and hydrolyzing the latter in an acid medium to obtain a compound of formula I.

In a modification of the process of the invention, the halohydrin of the formula

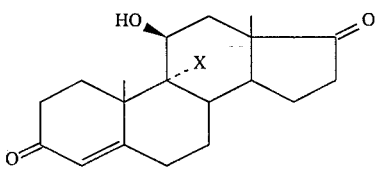

wherein X is defined as above is subjected to a rearrangement reaction in the presence of an alcohol to obtain, after treatment with an acid, the compound of the formula

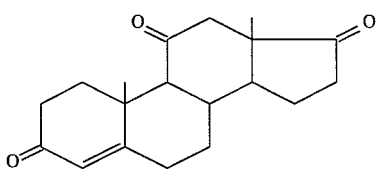

the 3-oxo function or the latter is selectively protected by the action of a thiol or a dithiol of the formula

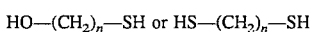

wherein n is defined as above to obtain a compound of the formula

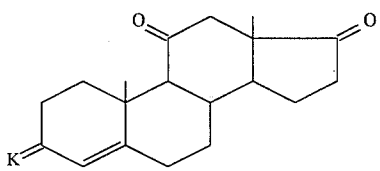

wherein K is defined above, the latter is reacted with a reagent of the formula $Hal_3C$—$CO_2R$ wherein Hal and R are defined as above and then the synthesis is continued as described previously.

In another variation of the process of the invention, a compound of formula II as defined above is reacted with a selective protection agent of the 3-oxo as defined above to obtain a compound of the formula

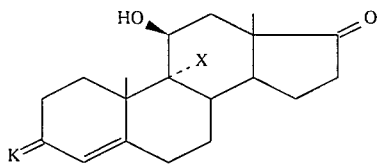

wherein X and K are defined as above, subjecting the latter to a rearrangement reaction in the presence of an alcohol to obtain, after treatment with an acid, a compound of formula IV as defined above, then said compound of formula IV is treated with a reagent of the formula

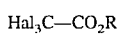

in which Hal and R are defined as above, and then the synthesis is continued as described above.

When R is alkyl, it is preferbly methyl, ethyl, propyl, isopropyl, butyl, sec-butyl, tert-butyl, pentyl or hexyl. When R is aralkyl, it is perferably benzyl or phenethyl. When R is silyl remainder, it is, for example, a trialkylsilyl remainder such as trimethylsilyl, tert-butyl dimethylsilyl, or also, triphenylsilyl or diphenyl tert-butylsilyl remainder.

When $R_a$ and $R_b$ are alkyl, they are selected preferably from ethyl, linear or branched propyl, linear or branched butyl or, preferably, methyl. When $R_a$ and $R_b$ are alkoxy, they may be ethoxy, linear or branched propoxy, linear or branched butoxy or, preferably, methoxy. In the compound of formula II, X is preferably bromine.

The rearrangement reaction of the halohydrin is preferably carried out in the presence of a higher alcohol or a polyalcohol, for example glycerol or a diol such as propylene glycol or, preferably ethylene glycol, used in excess, by heating to a temperature lower than 100° C. It may be advantageous to operate in the presence of a cosolvent, preferably with a boiling point lower than 100° C., at reflux of this cosolvent The cosolvent is an inert solvent under the reaction conditions, for example, ethyl acetate.

The acid treatment is carried out by an aqueous acid, for example, hydrochloric acid, hydrobromic acid or sulfuric acid. The protection of the 3-oxo function is carried out by the action of a dithiol in an acid medium, notably ethanedithiol in the presence of concentrated hydrochloric acid or hydrobromic acid, in a catalytic quantity, or in the presence of a Lewis acid such as zinc chloride, titanium tetrachloride or boron trifluoride, preferably in the form of the etherate.

Preferably the blocking of the 3-oxo function is carried out, and then the rearrangement of the halohydrin is carried out according to a so-called "one pot" method, that is to say without isolating the intermediate of formula V. The rearrangement of the halohydrin is facilitated by the intermediate blocking of the 3- or 3,17 oxo functions which allows the use of very gentle operating conditions.

It can be indicated, for information only, that the consequence of blocking appears to be the labilization of the carbon-halogen bond in position 9 which therefore facilitates the rearrangement.

The Lewis acid used in the reaction of the compound of formula IV with the trihaloacetate is, for example, zinc chloride, aluminium chloride, diethylaluminium chloride, or, preferably, titanium tetrachloride. In particular, an alkyl trihaloacetate is used and quite particularly methyl or ethyl trichloroacetate. The operation preferably takes place in a cyclic ether such as tetrahydrofuran or dioxane.

The action of the phenol on the compound of formula VI is carried out in the presence of a base which can be, for example, an alkali metal or alkaline-earth metal hydroxide or carbonate, particularly sodium, potassium, barium or calcium, a hydride, an alcoholate or an alkali metal amide, particularly sodium, potassium or lithium or an alkyl lithium, particularly butyl lithium. The operation takes place in an organic solvent such as a ketone like acetone or methylethyl ketone, if appropriate in a mixture with a halogenated solvent such as methylene chloride or with an ether such as dioxane or tetrahydrofuran.

Preferably in the process as defined above, the phenol is of the formula

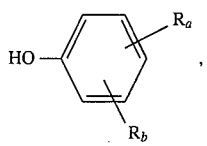

wherein $R_a$ and $R_b$ are hydrogen, hydroxy or methyl.

The reducing agent can be a metal hydride, preferably aluminium, for example the double lithium aluminium hydride of diethyl sodium aluminium hydride, diisobutyl aluminium hydride or also sodium dihydro bis(2-methoxyethoxy) aluminate. The operation takes place preferably in toluene or tetrahydrofuran. The reducing agent can also be an alkali metal borohydride, for example, sodium borohydride, catalyzed, if appropriate, by a lithium salt, or lithium borohydride.

The deprotection of the 3-oxo function is carried out by the action of iodine in the presence of a base such as an alkali metal bicarbonate, or by the action of iodine in a catalytic quantity in the presence of an oxidizing agent, preferably hydrogen peroxide, by the action of methyl iodide, glyoxylic acid, or also metal salts such as mercury or cadmium. Generally the operation takes place in a solvent such as a lower alkanol, for example, methanol or ethanol, in admixture with a halogenated solvent, for example, methylene chloride, in the presence of water.

The epoxidation agent can be a peracid such as metachloroperbenzoic acid, perphthalic acid, pertungstic acid or hydrogen peroxide used alone or in the presence of hexachloro- or hexa-fluoroacetone. The epoxidation agent can also be a hydroperoxide such as tert-butyl hydroperoxide used in the presence of the vanadium acetyl acetonate or other metals such as molybdenum in a catalytic quantity. The operation takes place in an organic solvent such as methylene chloride, carbon tetrachloride, chloroform, methanol, tetrahydrofuran, dioxane, toluene or ethyl acetate, if appropriate in the presence of water and can also take place in a buffered medium, for example, disodium phosphate or a trisodium phosphate-phosphoric acid mixture.

The hydrolysis of the epoxide in the 17,20-position is carried out by the action of an aqueous acid, the acid being, particularly a mineral acid such as hydrochloric acid, sulfuric acid or nitric acid can also take place in a buffered medium, such as those mentioned above.

The new synthesis of hydrocortisone of the invention presents a certain number of advantages, which are summarized as follows: The rearrangement leading from the 11-OH compound to the 11-keto compound via the intermediate halohydrin, is carried out under far more gentle conditions that those described in the European Patent No. 30,368, which presents an advantage both in the level of the reaction yield because the formation of secondary or degradation products is limited, and an advantage on the industrial level to the extent that the synthesis is more economical; The blocking in position 3 is remarkably selective in contrast to the known blockings by enol ethers and ketals which lead to mixtures of products blocked in positions 3 and 3,17; The blocking in the 3-position in the invention is very stable under the reaction conditions used whether they are acidic or basic, and its elimination during synthesis, notably by the action of iodine in a basic medium or iodine in catalytic quantity under gentle oxidizing medium, is very easy; Access to hydrocortisone is possible without going through a hydroxylation stage in the 11-position which is the case with known synthesis using androstenedione at the start. Accordingly, this improves the overall yield of the process.

Among the novel intermediates of the invention are the compounds of the formula

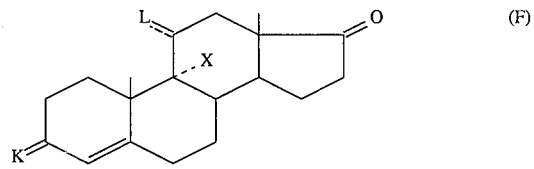

wherein K is a protective group of the oxo of the formula

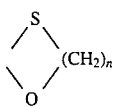

or preferably

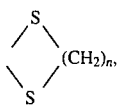

wherein n is 2 or 3 and particularly 2, and either L is oxo and the dotted line in the 11-position is a bond and X is hydrogen, or L is 11-hydroxy, the dotted line in 11-position is not a bond and X is chlorine, bromine or iodine and particularly bromine, the compounds of the formula

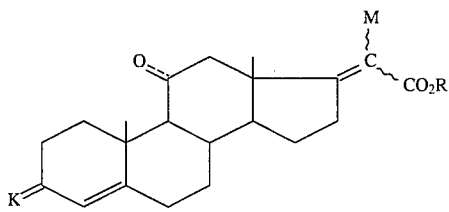

wherein K is a protective group of the oxo of the formula

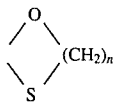

or preferably

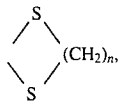

wherein n is 2 or 3 and particularly 2 and M is either chlorine or bromine and preferably chlorine or

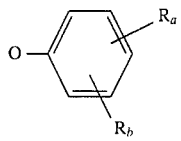

wherein $R_a$ and $R_b$ have the meaning above and are preferably hydrogen, hydroxy or methyl and R has the meaning above and preferably is methyl or ethyl as well as the compounds of the formula

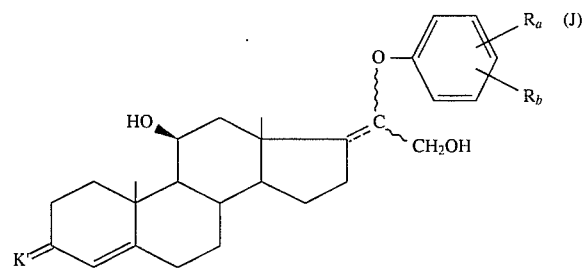

wherein either K' is oxygen or K, which is a protective group of the oxo of the formula

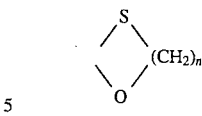

or preferably

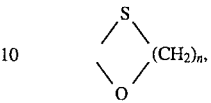

wherein n is 2 or 3 and preferably is 2, the dotted line in the 17-position is a bond, $R_a$ and $R_b$ have the above meaning and preferably are hydrogen, hydroxy or methyl, or K' is oxygen, the dotted line in 17-position is epoxy and $R_a$ and $R_b$ have the meaning above.

The compounds of formula II are described in particularly in U.S. Pat. No. 3,072,684.

In the following examples, there are described several preferred embodiments to illustrate the invention. However, it is to be understood that the invention is not intended to be limited to the specific embodiments.

EXAMPLE 1

Preparation of hydrocortisone
STEP A: Cyclic 3-[(1,2-ethanediyl)-mercaptole of $\Delta^4$-androstene-3,11,17-trione
a) $\Delta^4$-Androstene-3,11,17-trione.
  1.05 g of 9 α-bromo-$\Delta^4$-androstene-11β-ol-3,17-dione, 7.5 ml of ethyl acetate and 2.5 ml of ethylene glycol were mixed together at ambient temperature under an inert gas atmosphere. The mixture was refluxed with stirring for 10 hours, cooled and then 10 ml of 2N hydrochloric acid and 10 ml of water were added. The mixture was stirred for 20 hours, and then the ethyl acetate was eliminated under reduced pressure. After salting out with sodium chloride and cooling to 0° C., the crystals were separated, washed with water and dried. The crystals were taken up in methylene chloride, and after ethyl acetate was added, the methylene chloride was evaporated off. The solution was chilled and the crystals were separated, then dried to obtain 0.52 g of the expected product melting at 221° C. By extracting the aqueous phase with methylene chloride and chromatographing the crude product on silica, eluting with a methylene chloride-ethyl acetate (95-5) mixture, 0.097 g of the expected product were obtained, which after crystallization from ethyl acetate, melted at 220° C.
b) Cyclic 3-[(1,2-ethanediyl)-mercaptole] of $\Delta^4$-androstene-3,11,17-trione
  100 ml of methanol, 5 g of the product of Step A), 1.8 ml of ethane dithiol and 2.5 ml of boron trifluoride etherate were mixed together at ambient temperature under an inert gas atmosphere. After 90 minutes of stirring, the methanol was evaporated off. The residue was taken up in methylene chloride, washed with a saturated aqueous solution of sodium bicarbonate, with water, dried, then brought to dryness. The product obtained was crystallized from hexane to obtain 5.99 g of the expected product melting at 160° C.
  NMR Spectrum (CDCl$_3$ 90 MHZ ppm). 18—CH$_3$: 0.85; 19—CH$_3$: 1.27; thioketal: 3.17 to 3.47; H$_4$: 5.6
  IR spectrum (CHCl$_3$)
  Absence of $\Delta^4$ 3-one; absorptions at 1645 cm$^{-1}$ (C=C), 1709 cm$^{-1}$ (C=0 in 11-position), 1740 cm$^{-1}$ (C=0 in 17-position).

STEP A': Cyclic 3-[(1,2-ethanediyl)-mercaptole] of $\Delta^4$-androstene-3,11,17-trione.

4 g of 9 α-bromo-$\Delta^4$-androstene-11 β-ol-3,20-dione and 40 ml of ethyl acetate were mixed together under an inert gas atmosphere and then 0.9 ml of ethane dithiol were added at ambient temperature. Then 0.09 ml of 22° Be hydrochloric acid were added slowly and the mixture was stirred for 6 hours. Then 9.3 ml of ethylene glycol were introduced and the mixture was refluxed for 20 hours, then cooled to 20° C. The reaction mixture was poured into a mixture of 40 ml of 2N hydrochloric acid and 40 ml of water and after stirring for 16 hours, the ethyl acetate was eliminated under reduced pressure (20 mm/Hg) at 35° C. maximum. The suspension was then cooled to 0°, +5° C., stirred for 1 hour and the crystals were separated out. The crystals were washed with water, then dried and chromatographed on silica eluting with a hexane-dioxane (9-1) mixture to obtain 3.2 g of the expected product.

NMR Spectrum ($CDCl_3$ 300 MHz ppm): 18—$CH_3$: 0.84 (s); 19—$CH_3$: 1.26 (s); thioketal: 3.15 to 3.4; $H_4$: 5.57; skeleton: 1.1 to 2.61 (m)

IR Spectrum ($CHCl_3$)

Absorptions at 1741–1709 $cm^{-1}$ (ketches); 1641 $cm^{-1}$ (C=C)

STEP B: Methyl 20-chloro-3,3-[1,2-ethanediyl-bis(thio)]-$\Delta^{4,17}(20)$-pregnadien-11-one-21-oate 100 ml of tetrahydrofuran and 12.55 g of zinc powder were mixed together under an inert atmosphere and 7.9 ml of titanium tetrachloride, then a mixture of 100 ml of tetrahydrofuran, 8.6 ml of methyl trichloroacetate and 18 g of the product of Step A or A' were added slowly at −10°/−15° C. The temperature was allowed to return to ambient and then the mixture was stirred at ambient temperature for 90 minutes. Then, 100 ml of a water—pyridine (4-1) mixture was added at +10°/+15° C. and the mixture was stirred for 1 hour while allowing the temperature to rise. Then, 100 ml of a water—concentrated hydrochloric acid (6-4) mixture was added and the mixture was stirred for 15 minutes, followed by extraction with methylene chloride. The organic phase was washed with water, dried and the solvent was evaporated. The crystals were dissolved in methylene chloride and after isopropyl ether was added, the methylene chloride was evaporated, followed by cooling. The crystals were separated out and the mother liquors were chromatographed on silica eluting with a cyclohexane—ethyl acetate (8-2) mixture to obtain 21.8 g of the expected product melting at 175° C.

IR Spectrum ($CHCl_3$)

Absorptions at 1715 $cm^{-1}$ and 1730 $cm^{-1}$ (C=O) max. 1705 $cm^{-1}$ 1643 $cm^{-1}$ (C=C $\Delta^4$) and 1610 $cm^{-1}$ (C=C)

NMR Spectrum ($CDCl_3$ 90 MHz ppm)

Mixture of isomers 20 Cl 18—$CH_3$: 1.02–0.98; 19—$CH_3$: 1.25; thioketal: 3.33; $CH_3$-ester: 3.83–3.82; $H_4$: 5.58.

STEP C: Methyl 20-phenox-3,3-[(1,2-ethanediyl-bis(thio)] $\Delta^{4,17}(20)$-pregnadien-11-one-21-oate A mixture of 18 g of phenol, 150 ml of butanone, 30 g of the product of Step B and 17.7 g of potassium carbonate was refluxed under an inert atmosphere. After 16 hours, the mixture was poured into a mixture of 100 ml of water, 90 g of ice and 10 ml of 10N sodium hydroxide. Extraction took place with methylene chloride and the organic phase was washed with water and concentrated. After taking up the residue in methanol and allowing the solution to cool slowly, the crystals were separated and dried to obtain 27.4 g of the expected product melting at 208° to 210° C.

IR Spectrum ($CHCl_3$)

Absorption at 1592–1491 $cm^{-1}$ (Aromatic $C_6H_5$-O-type); 1714–1705 $cm^{-1}$ (C=O); 1646 $cm^{-1}$ (C=C)

NMR Spectrum ($CDCl_3$ 90 MHz ppm). 18—$CH_3$: 0.9; 19—$CH_3$: 1.21; thioketal: 3.33; $CH_3$ ester: 3.63; $H_4$: 5.58; $C_6H_5$: 6.81 to 7.39 Mixture of isomers 20-O—$C_6H_5$ STEP D: Cyclic (11β)-3,3-[(1,2-ethanediyl)-mercaptole] of 20phenoxy-$\Delta^{4,17}(20)$-pregnadien-11,21-diol-3-one 20 g of the product of Step C and 200 ml of toluene were mixed together under an inert gas atmosphere and after cooling to −25° C., 110 ml of a 20% solution of diisobutyl aluminium hydride in toluene were introduced slowly. The temperature was allowed to rise to 10° C. and the mixture was stirred for 1 hour. Then, the mixture was cooled to −15° C. and 10 ml of methanol were added slowly. The temperature was allowed to rise to 0° C. and 200 ml of 2N hydrochloric acid were added slowly. After decanting, the organic phase was washed with water, dried and the solvent was evaporated. The residue was chromatographed on silica eluting with a toluene—ethyl acetate (9-1) mixture to obtain 17.4 g of the expected product.

IR Spectrum ($CHCl_3$)

Absorption at 1490–1596 $cm^{-1}$ ($C_6H_5$—O—C); 1644 $cm^{-1}$ (C=C) $^{\Delta 4}$) and 1682 $cm^{-1}$ (C=C); 3612 $cm^{-1}$ (free OH)

NMR Spectrum ($CDCl_3$—$C_5D_5N$) (90 MHz ppm) 18—$CH_3$: 1.17; 19—$CH_3$: 1.29; thioketal: 3.33; $CH_2OH$: 4.15; $H_{11}$: 4.32; $H_4$: 5.45 were added and then 0.3 g of iodine. A pH of 1.5 ml was obtained and 1.4 ml of 50% hydrogen peroxide were introduced over 15 minutes. The oxidizing power was neutralized by the addition of 2 g of sodium thiosulfate and then 5 g of clarcel were added, followed by filtering and concentrating to dryness under reduced pressure. The dry extract was dissolved in methylene chloride, washed with a solution of 1 g of sodium thiosulfate in 25 ml of water, decanted, dried and concentrated to dryness under reduced pressure to obtain 4.8 g of the crude expected product. 1.8 g of this product was purified by chromatographing on silica (eluant: methylene chloride—isopropanol (97.5–2,5)) to obtain 1.7 g of the desired product melting at 188° C.

IR Spectrum ($CHCl_3$)

Absorptions at 3613 $cm^{-1}$ (OH); 1662, 1617 and 868 $cm^{-1}$ ($\Delta^4$-3-oxo); 1597–1491 $cm^{-1}$ (—O—$C_6H_5$)

NMR Spectrum ($CDCl_3$—$C_5D_5N$—90 MHz ppm) 18—$CH_3$: 1.17; 19—$CH_3Z$: 1.42; $H_{11}$: 4.27; $H_4$: 5.67; $CH_2OH$: 4.11; $C_6H_5$: 6.87 to 7.37

STEP F: 17,20-epoxy-20-phenoxy-$\Delta^4$-pregnadien-11β,21-diol-3-one 1.0 g of the product of Step E, 10 ml of ethyl acetate and 5 ml of water were mixed together under an inert gas atmosphere and 0.5 g of disodium phosphate, 0.65 g perphthalic acid and 0.75 ml of 50% hydrogen peroxide were added to the mixture. The mixture was stirred for 3 hours 15 minutes and after another 0.15 g of disodium phosphate and 0.20 g of perphthalic acid were added. The mixture was stirred for 75 minutes. Then 20 ml of ethyl acetate and 9 ml of 1N sodium hydroxide were added and the mixture was stirred for 5 minutes, followed by decanting. The organic phase was washed with water and with a water solution of sodium bisulfate and 1N sulfuric acid, dried and evaporated to dryness to obtain 1.05 g of the crude and unstable expected product which was used as is for the following step. Rf: 0.28 (silica—$CH_2Cl_2$/Dioxane-90/10).

IR Spectrum ($CHCl_3$)

Absorption at 3613 cm$^{-1}$ (OH); 1662 and 1616 cm$^{-1}$ ($\Delta^4$-3-one); 1600, 1590 and 1494 cm$^{-1}$ (aromatic)

NMR Spectrum ($CDCl_3$ 300 MHz ppm)

18—$CH_3$: 1.29 (s); 19—$CH_3$: 1.43 (s); —C—$CH_2$—O—: 3.49 (dd) and 4.20 (dd); $H_{11}$ eq.: 4.32; $H_4$: 5.68; H of O—$C_6H_5$: para 7.06 (t), ortho 7.13 (d) and meta 7.29 (t).

STEP G: Hydrocortisone 5 ml of methanol, 3 ml of water and 0.08 ml of 1N sulfuric acid (pH 2) were mixed together under an inert gas atmosphere and after 0.525 g of the product of Step F were added at ambient temperature, the mixture was stirred for 16 hours. The mixture was neutralized by the addition of sodium bicarbonate and extraction was carried out with methylene chloride. The organic phase was dried and evaporated to dryness. The residue was taken up in hot methylene chloride with 5% methanol, then concentrated until the start of crystallization. After cooling, the crystals were separated and dried. The mother liquors were concentrated and the residue was chromatographed on silica eluting with a methylene chloride-methanol (95-5) mixture to obtain in total 0.318 g of the expected hydrocortisone melting at 224° C. and having a specific rotation of $[\alpha]_D^{20}=+164°\pm2°5$ (C=1% in ethanol).

IR Spectrum (nujol)

Absorption at 3430 cm$^{-1}$ (OH), 1710 cm$^{-1}$ (C=0), 1642, 1630 and 1610 cm$^{-1}$ ($\Delta^4$-3-one).

Various modifications of the process of the invention may be made without departing from the spirit or scope thereof and it should be understood that the invention is intended to be limited only as defined in the appended claims.

What we claim is:

1. A compound of the formula

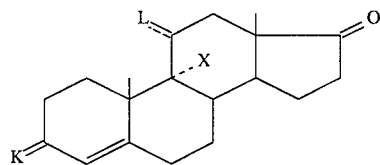

wherein K is a protective group of the oxo of the formula

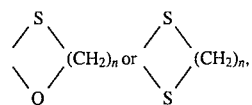

wherein n is 2 or 3 and L is a 11β-hydroxy, the dotted line in the 11-position is not a bond and X is chlorine, bromine or iodine.

* * * * *